US008052653B2

(12) United States Patent
Gratwohl et al.

(10) Patent No.: US 8,052,653 B2
(45) Date of Patent: Nov. 8, 2011

(54) NEEDLE PROTECTION DEVICE COMPRISING A DISTAL PROTECTION ELEMENT AND A PROXIMAL PROTECTION ELEMENT

(75) Inventors: Christian Gratwohl, Aarau (CH); Marc Lanz, Lobsigen (CH); Urs Widmer, Bern (CH); Martin Wymann, Liebefeld (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/399,700

(22) Filed: Mar. 6, 2009

(65) Prior Publication Data

US 2009/0254042 A1      Oct. 8, 2009

Related U.S. Application Data

(63) Continuation of application No. PCT/CH2007/000414, filed on Aug. 22, 2007.

(30) Foreign Application Priority Data

Sep. 6, 2006   (DE) .................. 10 2006 042 233

(51) Int. Cl.
*A61M 5/32* (2006.01)
*A61M 5/178* (2006.01)
(52) U.S. Cl. ........ 604/198; 604/192; 604/162; 604/163; 604/164.08
(58) Field of Classification Search .................. 604/110, 604/198, 192, 263, 506, 193–197, 162–163, 604/164.08
See application file for complete search history.

(56) References Cited

U.S. PATENT DOCUMENTS

| | | | | |
|---|---|---|---|---|
| 4,664,654 | A | * | 5/1987 | Strauss .................. 604/198 |
| 5,030,209 | A | * | 7/1991 | Wanderer et al. ............. 604/198 |
| 7,521,022 | B2 | * | 4/2009 | Konrad .................. 422/103 |
| 2001/0031949 | A1 | * | 10/2001 | Asbaghi .................. 604/198 |
| 2003/0014018 | A1 | * | 1/2003 | Giambattista et al. ........ 604/198 |

FOREIGN PATENT DOCUMENTS

| | | |
|---|---|---|
| WO | 01/91837 A1 | 12/2001 |
| WO | 01/93924 A1 | 12/2001 |
| WO | 03/045480 A1 | 6/2003 |
| WO | 2004/030539 A1 | 4/2004 |

* cited by examiner

*Primary Examiner* — Kevin C Sirmons
*Assistant Examiner* — Bradley Thomas, Jr.
(74) *Attorney, Agent, or Firm* — Dorsey & Whitney LLP; David E. Bruhn, Esq.

(57) ABSTRACT

A needle protection device detachably fixed to an injection appliance includes a needle, a needle holder from which a needle injection section of the needle projects distally and a needle connection section of the needle projects proximally, a distal needle protection element connected to the needle holder movable in the distal direction from a release position to a protection position and arranged behind the needle injection section in the release position and overlapping the needle injection section and distal end of the injection needle in the protection position, a proximal needle protection element connected to the needle holder movable from a release position and arranged behind the needle connection section into a protection position and overlapping the needle connection section and proximal end of the injection needle, and a blocking device which blocks movement of the proximal needle protection element from the protection position into the release position.

23 Claims, 13 Drawing Sheets

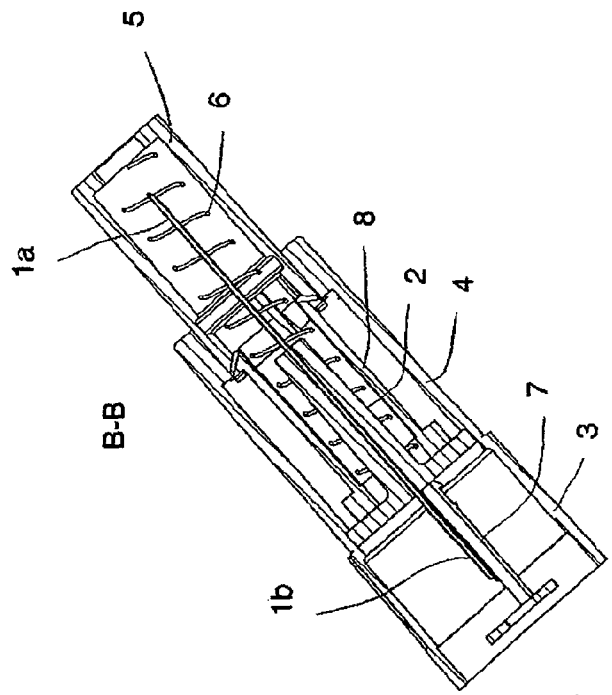
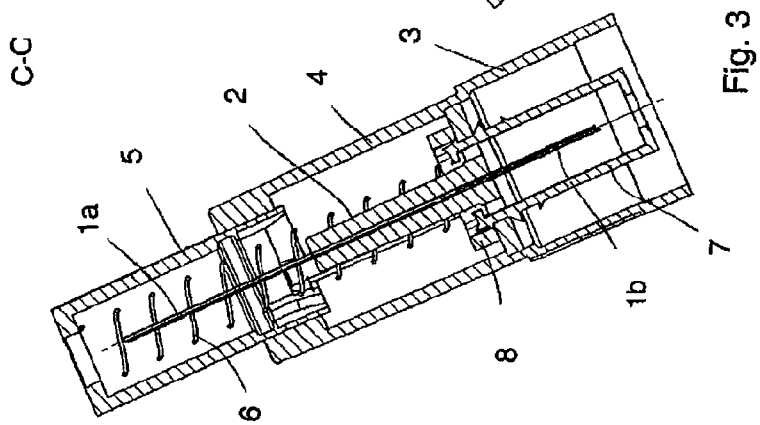
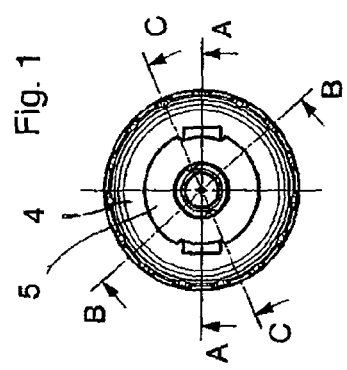
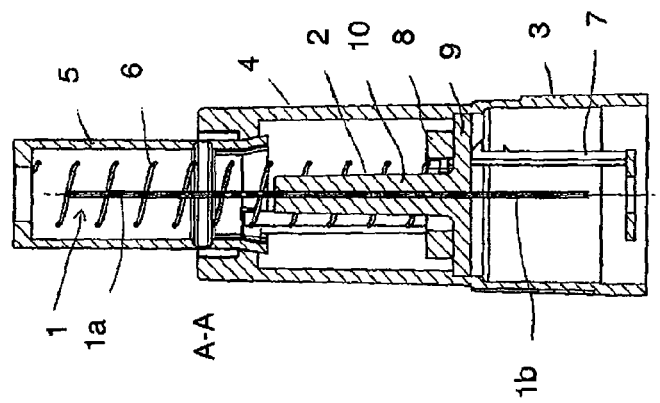

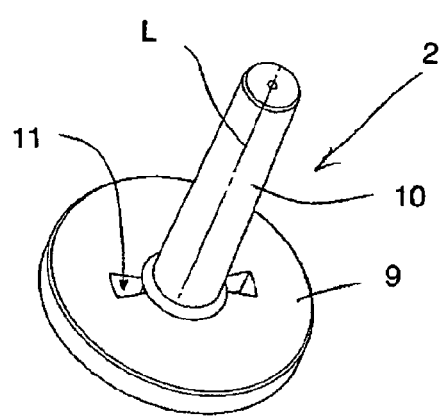
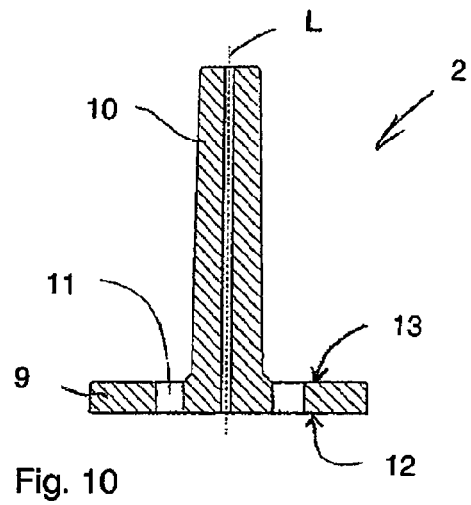
Fig. 9    Fig. 10
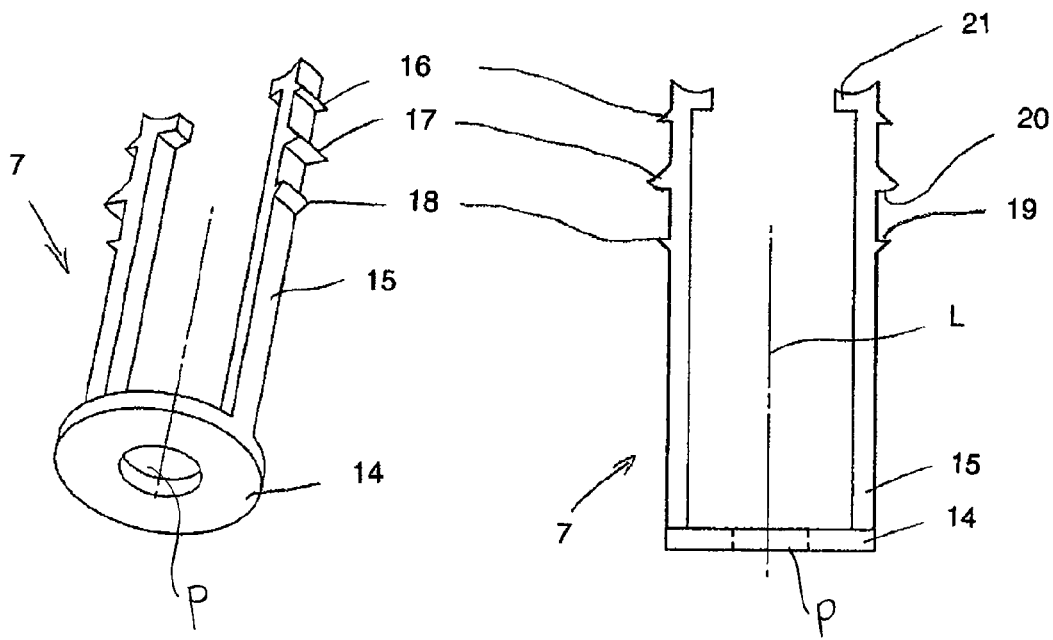
Fig. 11    Fig. 12

Fig. 19
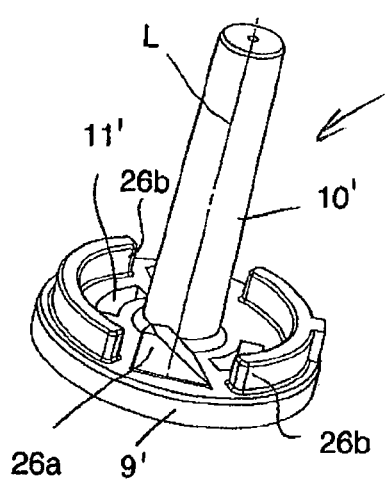
Fig. 20
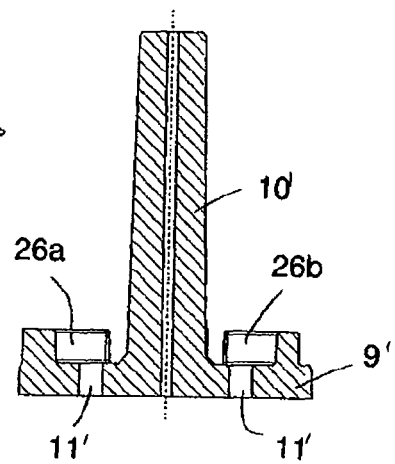
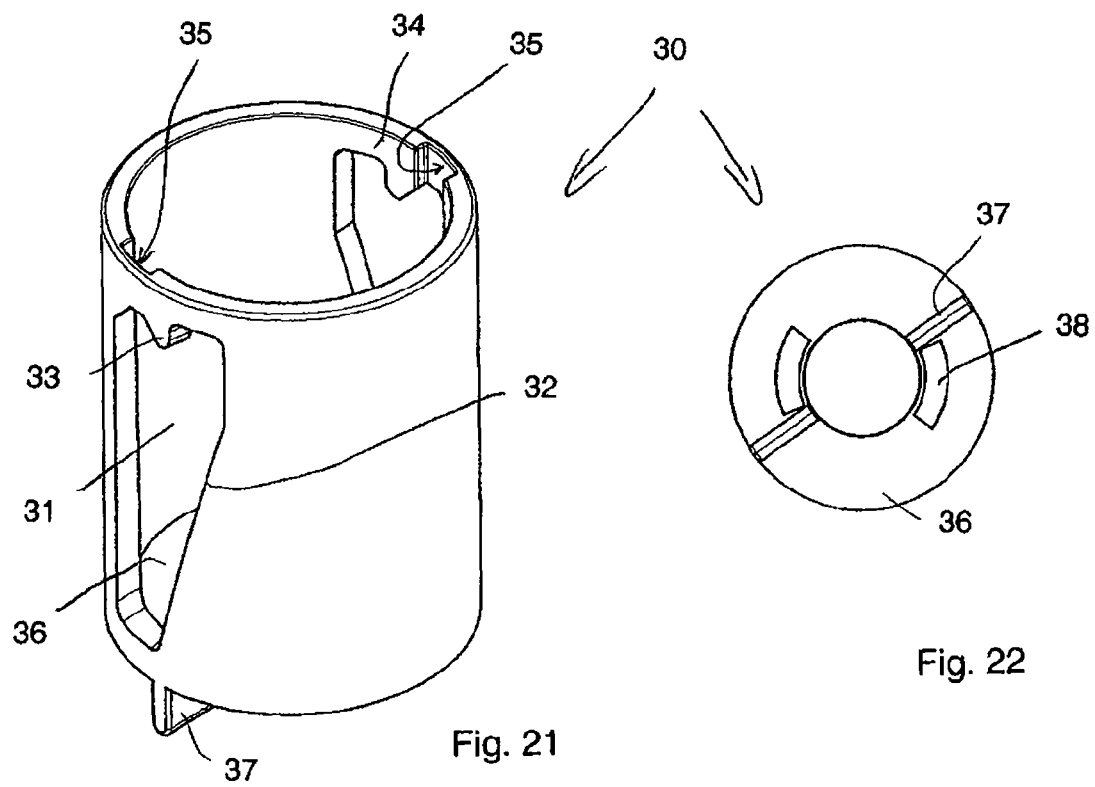
Fig. 21
Fig. 22

NEEDLE PROTECTION DEVICE COMPRISING A DISTAL PROTECTION ELEMENT AND A PROXIMAL PROTECTION ELEMENT

CROSS-REFERENCED RELATED APPLICATIONS

This application is a continuation of International Patent Application No. PCT/CH2007/000414 filed Aug. 22, 2007, which claims priority to German Patent Application No. DE 10 2006 042 233.3 filed Sep. 6, 2006, the entire contents of both of which are incorporated herein by reference.

BACKGROUND

The invention relates to devices for injecting, delivering, infusing, dispensing or administering a substance, and to methods of making and using such devices. More particularly, it relates to a needle guard device which is releasably attached to or can be attached to an injection device. The injection device may be used to administer medicaments, for example insulin, and for self-administration, i.e. by patients who administer the relevant medicament themselves. The injection device may be configured for repeated use and to allow the dose of product to be administered to be set or selected. More particularly, the injection device may be an injection device of the type used to treat diabetes or otherwise.

To prevent the risk of infections, needle guard devices have been developed which enable an injection device to be used only once. A needle guard device of this type is known from patent specification WO 01/91837 A1, for example. The injection needle extends through the needle holder and is fixedly secured by the needle holder. It has an injection portion extending beyond the needle holder in the distal direction and a connecting portion extending beyond the needle holder in the proximal direction.

SUMMARY

One object of the present invention is to provide needle guard devices that increase the level of safety which can be achieved by using such devices and to prevent injury due to piercing.

In one embodiment, the present invention comprises a needle guard which can be releasably attached to an injection device. In one embodiment, the needle guard comprises an injection needle and a needle holder holding the injection needle, from which the needle projects by a needle injection portion in the distal (front or forward) direction and from which the needle projects by a needle connecting portion in the proximal (rear) direction. The needle guard also has a distal needle guard for the needle injection portion which is connected to the needle holder so that it can move. The injection needle may extend through the needle holder and is fixedly secured by the needle holder. Alternatively, the needle injection portion and the needle connecting portion may also be separate needles, which are retained by the needle holder and connected to one another to establish a fluid flow. However, the needle holder may also incorporate the two needle portions in a single piece.

When administering the substance or product to be administered, the needle injection portion pierces the skin and/or tissue lying subcutaneously underneath. When a membrane is attached, providing a tight seal at a distal outlet of a reservoir filled with the product to be administered, the needle connecting portion pierces it. The distal needle guard is able to move in the distal direction relative to the needle holder from a released position as far as a guard position, such as by spring force. When the needle guard assumes the released position, the injection needle sits or rests with its needle injection portion beyond the needle guard in the distal direction. In the guard position, on the other hand, the needle guard overlaps the needle injection portion as far as and including a distal (forward or injection end) end of the injection needle. In the initial state prior to using the device for the first time, the needle guard may assume a distal initial position from which it can be moved into the released position.

In some embodiments, the distal needle guard is locked in the guard position so that it can not be moved into the released position again. The lock may be established automatically when the needle guard has reached the guard position, having moved in the distal direction. Apart from self-locking needle guard devices of this type, however, the present invention also generally relates to needle guard devices with a displaceable distal needle guard which does not lock after an injection. In such designs, the needle guard is primarily used to block the view to remove the fear of the injection needle for a user administering the product himself.

As provided herein, in some embodiments, the needle guard device comprises a proximal needle guard, which is displaceably connected to the needle holder. The proximal needle guard can be moved in the proximal direction out of a released position as far as a guard position. In the released position, the needle connecting portion extends beyond the proximal needle guard in the proximal direction. In the guard position, the proximal needle guard overlaps the needle connecting portion up to and including the proximal end of the injection needle. The needle guard device also has a lock mechanism for the proximal needle guard. As soon as the proximal needle guard has reached the guard position, having moved in the proximal direction, it is automatically locked by the lock mechanism so that it is no longer able to move back into the released position. Although needle guard devices with a distal guard are already known from the prior art, for example, from patent specification WO 01/91837 A1 mentioned above, as recognized herein, the needle connecting portion can also cause piercing injuries after the respective needle guard device has been used and the embodiments disclosed herein eliminate this risk via the other needle guard which automatically locks in a guard position after the needle guard device in accordance with the present invention has been used, i.e. as the injection device is removed or after it has been removed.

In some embodiments, the needle guard device has a fixing mechanism configured as a fixing sleeve to provide a releasable connection to the injection device. The fixing mechanism may co-operate with fixing means associated with or disposed externally on the injection pen. It may be a threaded or bayonet sleeve or a snap-fit, catch-fit or clip-on sleeve, for example. In such designs, the fixing device surrounds the needle connecting portion in a manner conventionally used for needle guard devices. However, the known fixing devices are usually so large in terms of their diameter that the user can easily reach the needle tip of the needle connecting portion with the finger and injure himself. The distal needle guard provided herein, however, is disposed closer to the needle connecting portion than with other fixing mechanisms, and the distance measured transversely to the needle connecting portion is short, such that the user does not come into contact with the proximal needle tip if he touches the proximal end of the proximal needle guard. As a result, the manufacturer also has greater freedom in terms of the design of the fixing mechanism because it offers an additional protective function compared with the other sleeve-shaped, fixing mechanisms, but in this case protecting against piercing injuries can be obtained by the proximal needle guard.

In some embodiments, a needle guard device in accordance with the present invention has a spring element, which biases the proximal needle guard in the proximal direction by a spring force. The spring element may be supported directly on the proximal needle guard but may also act on the needle guard via one or more intermediate elements. In such designs, when the needle guard device is removed from the injection device, the needle guard is moved into the guard position by spring force. In other variants, the same spring element also acts in the distal direction on the distal needle guard directly or via one or more intermediate elements. In further embodiments, the spring element is supported at one end on the distal needle guard and at the oppositely lying end on the proximal needle guard. Depending on its function, the spring element may be a compression spring, such as a helical spring. In alternative embodiments, the proximal needle guard is not moved into the guard position by spring force, but by a retaining mechanism comprising a retaining holder on the proximal needle guard and a retaining holder on the injection device or product reservoir, which automatically move into a retaining engagement when the needle guard device and injection device are connected, which causes the proximal needle guard to be moved from the released position into the guard position when the needle guard device is released. Once the proximal needle guard has assumed its guard position, the retaining engagement automatically releases when the needle guard device is substantially or completely detached from the injection device.

In some embodiments, the lock mechanism comprises at least two locking elements, a first locking element formed on the needle holder or, in the situation where the parts are separate, connected to the needle holder, and a second locking element formed on the proximal needle guard or, in the situation where the parts are separate, connected to the needle guard. At least one of the locking elements may be able to move transversely to the longitudinal direction of the injection needle against a resistant or rebounding spring force. The relevant locking element itself may be inflexible, i.e. rigid, and in such embodiments is biased by the rebounding spring force by a separate spring element. However, the relevant locking element may be elastic and may form an elastic bending beam. The rebounding spring force may be used to move the locking element into the locked engagement with the other locking element. The locked engagement may be achieved by an elastic snapping movement. In alternative embodiments, however, the lock mechanism may be provided in the form of only rigid locking elements, i.e. they are not flexible. This being the case, however, the locking elements may need to be moved into the locked engagement when the proximal needle guard moves into the guard position. In such embodiments, the lock mechanism may have one or more slide guides, by which the locking elements are forcibly guided relative to one another into the locked engagement.

In some embodiments, the second locking element formed on the proximal needle guard or connected to the needle guard may be guided outwardly from the needle guard and co-operate with the first locking element by gripping the needle guard device, but the proximal needle guard may extend through the needle holder in the distal or in the proximal direction, at least in the guard position.

In one embodiment, the proximal needle guard assumes a proximal (rearward) initial position prior to using the needle guard device, from which it is moved into the released position as the needle guard device is connected to the injection device. In a second embodiment, the proximal needle guard is already in the released position in the state in which the needle guard device is sold. In both embodiments, the needle guard device comprises an unlocking element. In the first embodiment, the unlocking element co-operates with the at least one locking element, which can be displaced transversely to the longitudinal direction of the injection device so that the locked engagement can be established during the movement out of the proximal initial position into the released position because the unlocking element is engaged with the transversely moving locking element, which may also include the situation in which it is engaged with the first and the second locking element in order to prevent the locked engagement. During the course of the injection, such as during piercing by the needle injection portion or as the needle injection portion is being pulled out of or has been pulled out of the tissue, the engagement between the unlocking element and locking element is automatically released so that the locking elements are able to move into the locked engagement when the needle guard device is detached from the injection device. In the second embodiment, during piercing by the injection needle, the unlocking element is moved out of an unlocking position, in which it prevents the proximal needle guard from moving in the proximal direction, into a neutral position in which it permits such a movement and hence a movement into the guard position. The unlocking element of the second embodiment may be rotatable and connectable to the needle holder so as to be rotatable about the injection needle.

The unlocking elements of both embodiments may be coupled with the distal needle guard or may be automatically coupled with the distal needle guard during piercing or as the injection needle is being pulled out of the tissue. In such designs, the distal needle guard causes the unlocking element to move out of the unlocking position into the neutral position via the coupling. The coupling may be a driving engagement by which the distal needle guard drives the unlocking element with it as far as the neutral position as it moves in the distal direction, i.e. during removal from the tissue. Alternatively, the slide guide may form the coupling, in which case the slide guide converts the piercing movement or the movement of extracting the distal needle guard into the movement of the unlocking element out of the unlocking position into the neutral position. As a result, the slide guide enables a linear piercing movement or extraction movement of the distal needle guard to be converted into a rotating movement of the unlocking element, for example.

BRIEF DESCRIPTION OF THE DRAWINGS

FIG. 1 is a view onto a distal end face of an example of a needle guard device according to a first embodiment in accordance with the present invention;

FIG. 2 shows the needle guard device in a longitudinal section A-A;

FIG. 3 shows the needle guard device in a longitudinal section B-B;

FIG. 4 shows the needle guard device in a longitudinal section C-C;

FIG. 9 is a perspective diagram showing a needle holder of the needle guard device;

FIG. 10 shows the needle holder in longitudinal section;

FIG. 11 is a perspective diagram showing a proximal needle guard of the needle guard device;

FIG. 12 shows the proximal needle guard in longitudinal section;

FIG. 19 is a perspective diagram showing a needle holder of the second embodiment;

FIG. 20 shows the needle holder of the second embodiment in longitudinal section;

FIG. 21 is a perspective diagram showing an unlocking element of the second embodiment;

FIG. 22 is a plan view in the distal direction showing the unlocking element of the second embodiment;

DETAILED DESCRIPTION

Figure 5:
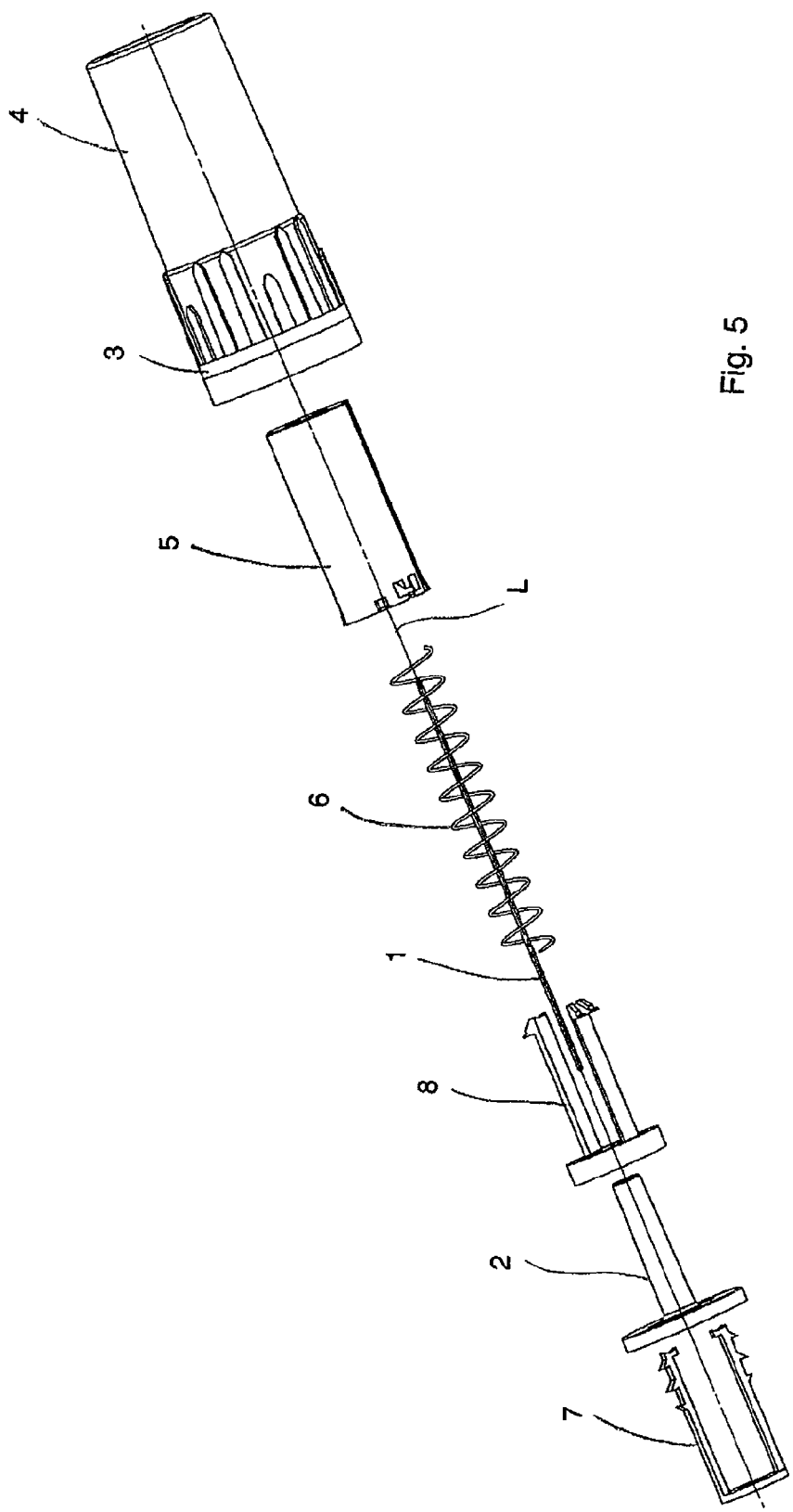
FIG. 5 illustrates components of the needle guard device aligned along a longitudinal axis of the needle guard device.
Figure 6:
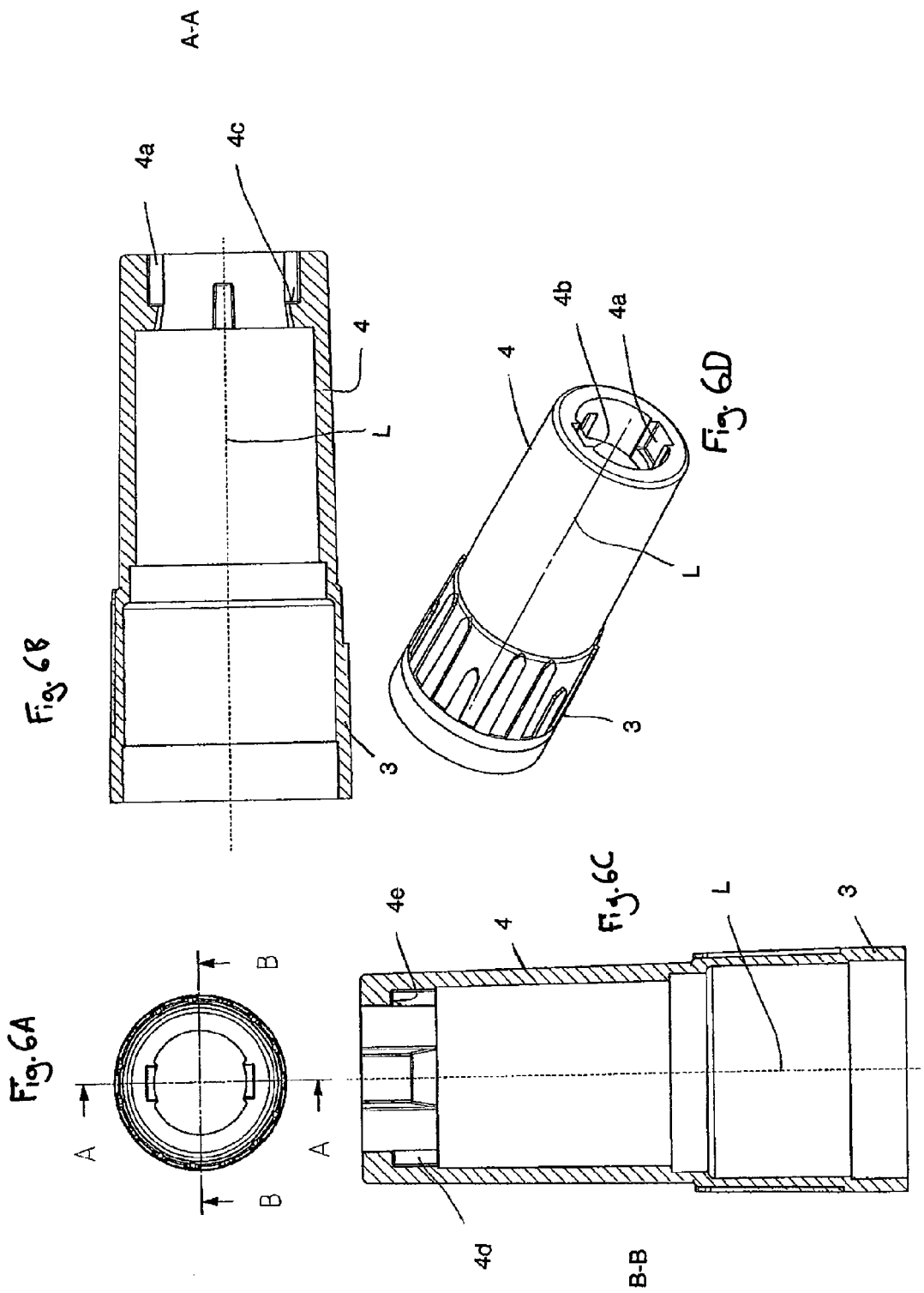
FIGS. 6A-D show a fixing and guide mechanism of the needle guard device at a front view, along longitudinal sections A-A and B-B and a perspective view along a longitudinal axis of the fixing guide mechanism.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc. Generally, unless otherwise indicated, relative positional or orientational terms (e.g., upwardly, downwardly, above, below, etc.) are intended to be descriptive, not limiting.

FIG. 1 is a plan view onto a distal end face illustrating a needle guard device based on a first embodiment of the present invention. Three longitudinal planes are indicated, A-A, B-B and C-C.

FIG. 2 is a view in longitudinal section A-A indicated in FIG. 1, showing the needle guard device based on the first embodiment. FIG. 3 is a view of the needle guard in longitudinal section B-B and FIG. 4 illustrates longitudinal section C-C.

FIGS. 1 to 4 illustrate the needle guard device in an initial state, which it assumes or is in prior to being used for the first time. In this state, the needle guard device may be supplied to the user in a suitable sterile packaging, not illustrated. The needle guard device comprises an injection needle 1 in the form a straight, hollow cannula and a needle holder 2, which fixedly retains the injection needle 1 in a middle needle portion so that the injection needle 1 is not able to move axially, i.e. in the longitudinal direction L, and is also not able to rotate. The needle holder 2 has a base 9 and a retaining region 10, which projects centrally out from the base 9 and holds the injection needle 1. The injection needle 1 extends through the retaining region 10 of the needle holder 2. It projects beyond the retaining region 10 by an injection portion 1a in the distal direction and by a connecting portion 1b in the proximal direction.

The needle holder 2 is inserted in a sleeve-shaped fixing and guide mechanism and secured so that it is not able to move. The needle holder 2 divides the fixing and guide mechanism into a proximal fixing portion 3 and a distal guide portion 4. The needle injection portion 1a extends beyond the guide portion 4 in the distal direction by a length suitable for administering subcutaneous injections. The fixing portion 3 constitutes a fixing mechanism to provide a releasable attachment to a distal end of an injection device. The fixing mechanism may have one or more catch elements to provide a catch connection to the injection device. Alternatively, the fixing mechanism of the needle guard device may also have a screw thread or a bayonet fitting. The fixing portion 3 surrounds the needle connecting portion 1b and extends beyond it in the proximal direction. The guide portion 4 acts as a non-rotatable, axial guide for a distal needle guard 5, which in the initial state assumes a distal initial position relative to the needle holder 2 in which it extends beyond the guide portion 4 and distal tip of the injection needle 1. The distal needle guard 5 is a sleeve-shaped body extending circumferentially around the injection portion 1a and simultaneously also acts as a visual guard so that the user is not able to see the injection portion 1a. The distal needle guard 5 is biased by a spring element 6 by spring force acting in the distal direction. In the distal initial position, the distal needle guard 5 is retained against the force of the spring element 6 relative to the guide portion 4 by an unlocking element 8.

FIGS. 5 to 8 illustrate how the distal needle guard 5 co-operates with the unlocking element 8 and the guide portion 4. In FIG. 5, the components of the needle guard device are aligned one after the other along its central longitudinal axis L in the order in which they are assembled. The injection needle 1 is shown released from the needle holder 2 but may already be fixedly connected to the needle holder 2 at the time of assembly.

FIGS. 6A-D shows the fixing and guide mechanism (which may be thought of as comprising elements 3, 4) from a front view (FIG. 6A), two longitudinal sections A-A (FIG. 6B) and B-B (FIG. 6C) and a perspective view (FIG. 4D). The fixing and guide mechanism has two recesses 4a in its guide portion 4 at the distal end in an internal face extending circumferentially about the longitudinal axis L. At their proximal end, the recesses 4a merge into the internal face via a steep shoulder. The two shoulders each form a translation stop 4c pointing in the distal direction. Disposed to the side of the recesses 4a are respective axially extending guides 4b to ensure that the distal needle guard 5 is guided in a straight line. Two other recesses 4d are provided at the distal end of the guide portion 4 in the same internal face, which are offset from the recesses 4a on the circumference of the internal face by 90° in each case. The recesses 4d each merge into the internal face via a steep shoulder at their distal end. The two shoulders each form a translation stop 4e pointing in the proximal direction.

Figure 7:
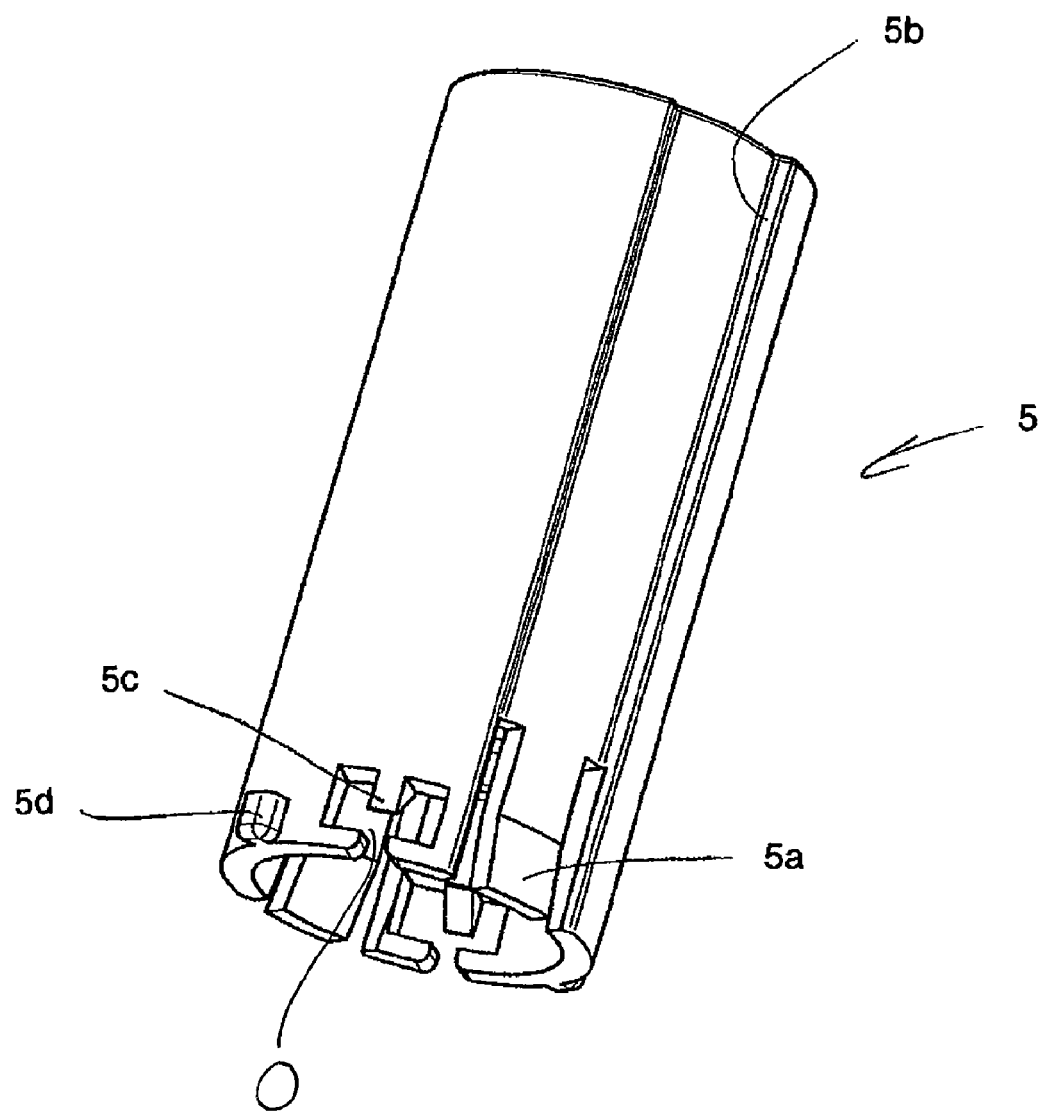
FIG. 7 shows a distal needle guard of the needle guard device.

FIG. 7 shows the distal needle guard 5. The distal needle guard 5 has axial guides 5b, which co-operate with the guides 4b of the guide portion 4 and with them guide the distal needle guard 5 linearly but prevent it from rotating. Disposed at the proximal end of the distal needle guard 5, two orifices O are provided in its casing, offset from one another in the circumferential direction by 180°. A projection 5c projects respectively in the proximal direction into the orifices O, which axially lengthens the casing of the distal needle guard 5 in the respective orifice. The internal faces of the projections 5b are outwardly inclined in the proximal direction towards free ends of the projections 5b and, in the embodiment illustrated as an example, each has a constant inclination. They each form a ramp in co-operation with the unlocking element 8. The distal needle guard 5 has two locking element elements 5a on its proximal end offset from one another in the circumferential direction by 180°, which are provided in the form of resilient lugs in the embodiment illustrated as an example. The locking elements 5a are outwardly inclined in the proximal direction. Finally, two locating elements 5d in the form of outwardly projecting cams are provided on the external circumference of the distal needle guard 5, likewise at its proximal end offset from one another by 180° in the circumferential direction.

Figure 8:
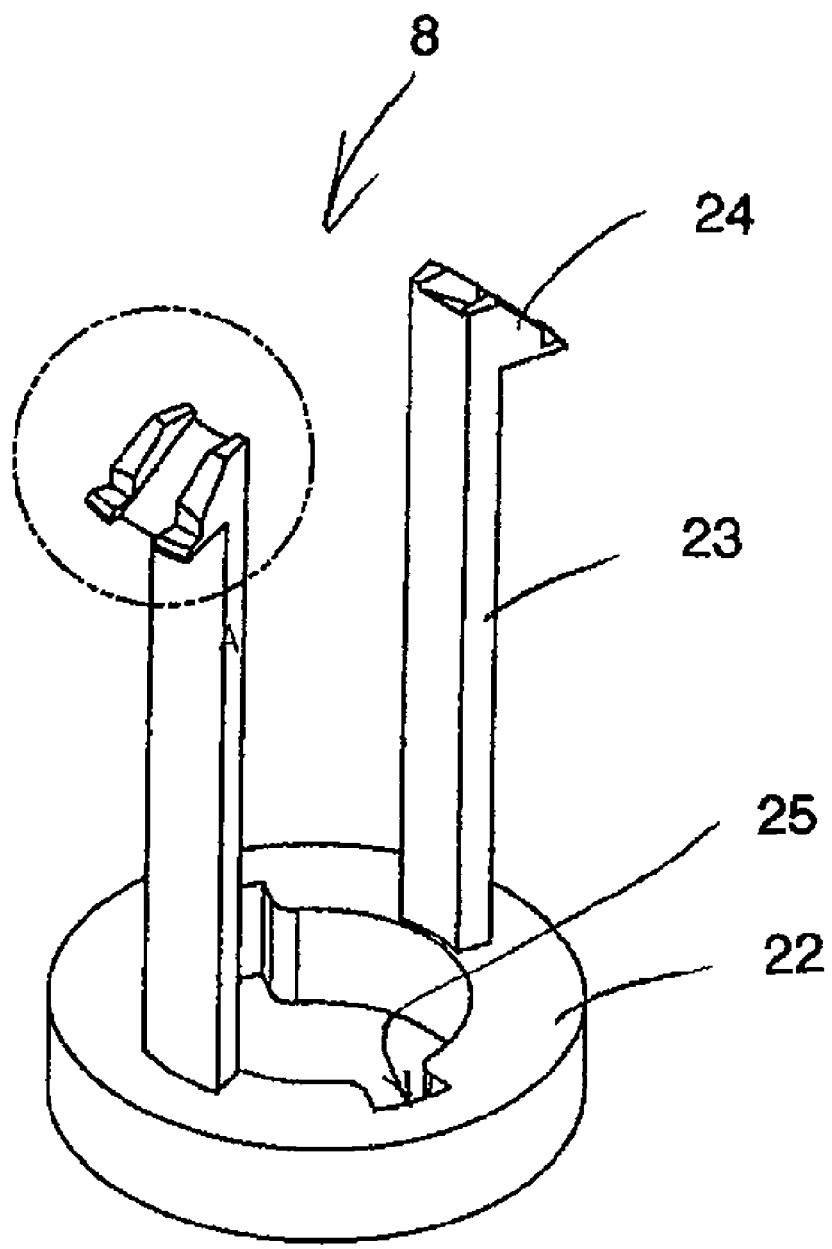
FIG. 8 shows an unlocking element of the needle guard device.

FIG. 8 illustrates an embodiment of the unlocking element 8. The unlocking element 8 has an annular base 22 at its proximal end. Projecting out from the base 22 in the distal direction are two fingers 23, each of which has a projection 24 extending outwardly from its distal end. When the needle guard device is in the initial state, the projections 24 extend through the orifices of the distal needle guard 5, as illustrated in FIG. 4, and hold the distal needle guard 5 in its distal initial position against the spring force of the spring element 6 due to the spring element 6 pushing the outer ends of the projections 24 into abutment with contact surfaces of the guide portion 4. Like the projections 5c of the distal needle guard 5, the projections 24 are inclined to form a ramp shape and their inclination is adapted to that of the projections 5c.

As may be seen from FIGS. 2 to 4, not only does the needle guard device have the distal needle guard 5, it also has a proximal needle guard 7 for the connecting portion 1b of the injection needle 1. The unlocking element 8 co-operates with both the distal needle guard 5 and the proximal needle guard 7. In co-operation with the distal needle guard 5, it fulfils the described locking function. In co-operation with the proximal needle guard 7, it fulfils an unlocking function because in its initial position illustrated in FIGS. 2 to 4, it prevents a movement of the proximal needle guard 7 in the distal direction from being blocked. To enable co-operation with the proximal needle guard 7, two axially extending recesses formed as an axially extending track 25 are provided in the internal face of the base 22 of the unlocking element 8 offset from one another in the circumferential direction by 180°, in which the proximal needle guard 7 locates in its initial position.

FIGS. 9 and 10 illustrate the needle holder 2 and FIGS. 11 and 12 illustrate the proximal needle guard 7. The proximal needle guard 7 has an annular base 14 at its proximal end and locking elements 15 projecting out from the base 14 in the distal direction. The locking elements 15 are finger-shaped or rod-shaped. In the embodiment illustrated as an example, these are two locking elements which project out from a distal end face of the base 14 and are offset from one another by 180° in the circumferential direction about the longitudinal axis L so that they enclose the needle connecting portion 1b between them when the proximal needle guard 7 is in the proximal initial position. The base 14 has a central passage P for the needle connecting portion 1b.

Disposed in a distal portion of the proximal needle guard 7, the locking elements 15 have several projections, each extending outwards from the locking elements, in this example three projections 16, 17 and 18. The locking elements 15 also each have a support 21 for the spring element 6. The supports 21 are formed by projections extending radially inwardly toward one another at the distal ends of the locking elements 15. The spring element 6 is supported on the proximal needle guard 7 in the proximal direction by means of the supports 21, in other words is clamped or held between the distal needle guard 5 and the proximal needle guard 7.

In the assembled state, the base 14 of the proximal needle guard 7 is disposed proximally of the base 9 of the needle holder 2 and the rod-shaped or finger-shaped locking elements 15 extend in the distal direction through two passages 11 formed in the base 9 of the needle holder 2. In the proximal initial position, the distal projections 16 absorb the force of the spring element 6. To this end, the projections 16 respectively form a stop pointing in the proximal direction which is pushed by the spring element 6 against a complementary stop 13 (FIG. 10) of the needle holder 2, which is formed by the base 9 of the needle holder 2 in the embodiment illustrated as an example. The projection 17 acts as another stop 20 pointing in the proximal direction. The projection 18 acts as yet another stop 19 but pointing in the distal direction.

Figure 13:
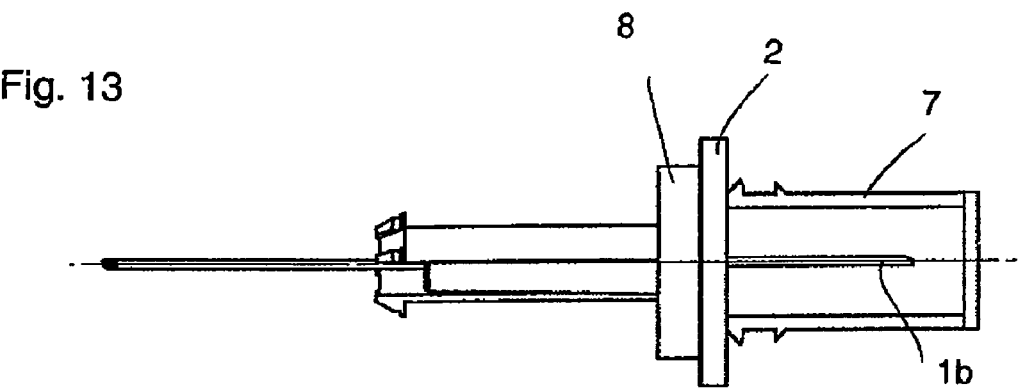
FIG. 13 shows an embodiment of a lock mechanism of the needle guard device, with the proximal needle guard in a proximal initial position.
Figure 14:
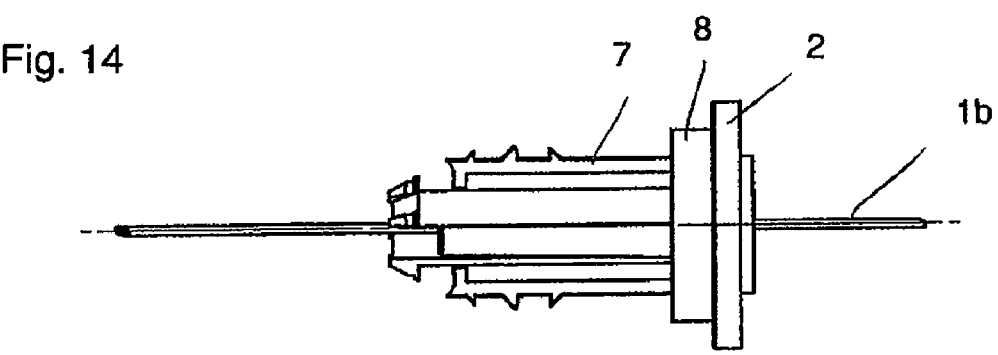
FIG. 14 shows the lock mechanism, with the proximal needle guard in a releasing position.
Figure 15:
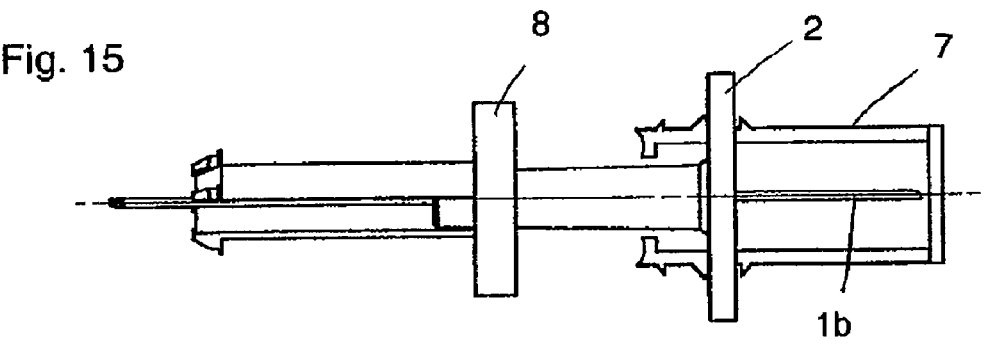
FIG. 15 shows the lock mechanism, with the proximal needle guard in a guard position.

FIGS. 13, 14 and 15 illustrate the different positions which the proximal needle guard 7 assumes relative to the needle holder 2 when the needle guard device is connected to the injection device and when detached from the injection device again after an injection. In FIG. 13, the proximal needle guard 7 has assumed its proximal initial position. It can be moved from the initial position against the force of the spring element 6 relative to the needle holder 2 and to the unlocking element 8 disposed in an unlocking position as far as a releasing position illustrated in FIG. 14, in which the needle connecting portion 1b extends beyond the proximal needle guard 7 in the proximal direction. In FIG. 15, the proximal needle guard 7 has assumed a guard position in which it is locked relative to the needle holder 2 so that it can not be moved out of the guard position back into the releasing position. To produce the lock, the needle holder 2 and the proximal needle guard 7 form a lock mechanism with locking elements in a locked engagement, namely on the two locking elements 15 of the proximal needle guard 7 and the base 9 of the needle holder 2 acting as a locking element. A result, the proximal needle guard 7 can be moved into the releasing position once only, namely by a force expended on the proximal needle guard 7 in the distal direction, and automatically moves due to the spring force of the spring element 6, as the external force decreases, back in the proximal direction as far as the locked guard position. In the guard position, it extends beyond the distal tip of the needle connecting portion 1b in the distal direction and thus protects the user against injuries caused by piercing. In the embodiment illustrated as an example, a particularly reliable guarding action is provided due to the annular base 14 of the proximal needle guard 7, the central passage of which is so narrow that the connecting needle is able to fit through the passage when attached to the injection device but the user cannot reach the distal needle tip through the passage.

Figure 16:
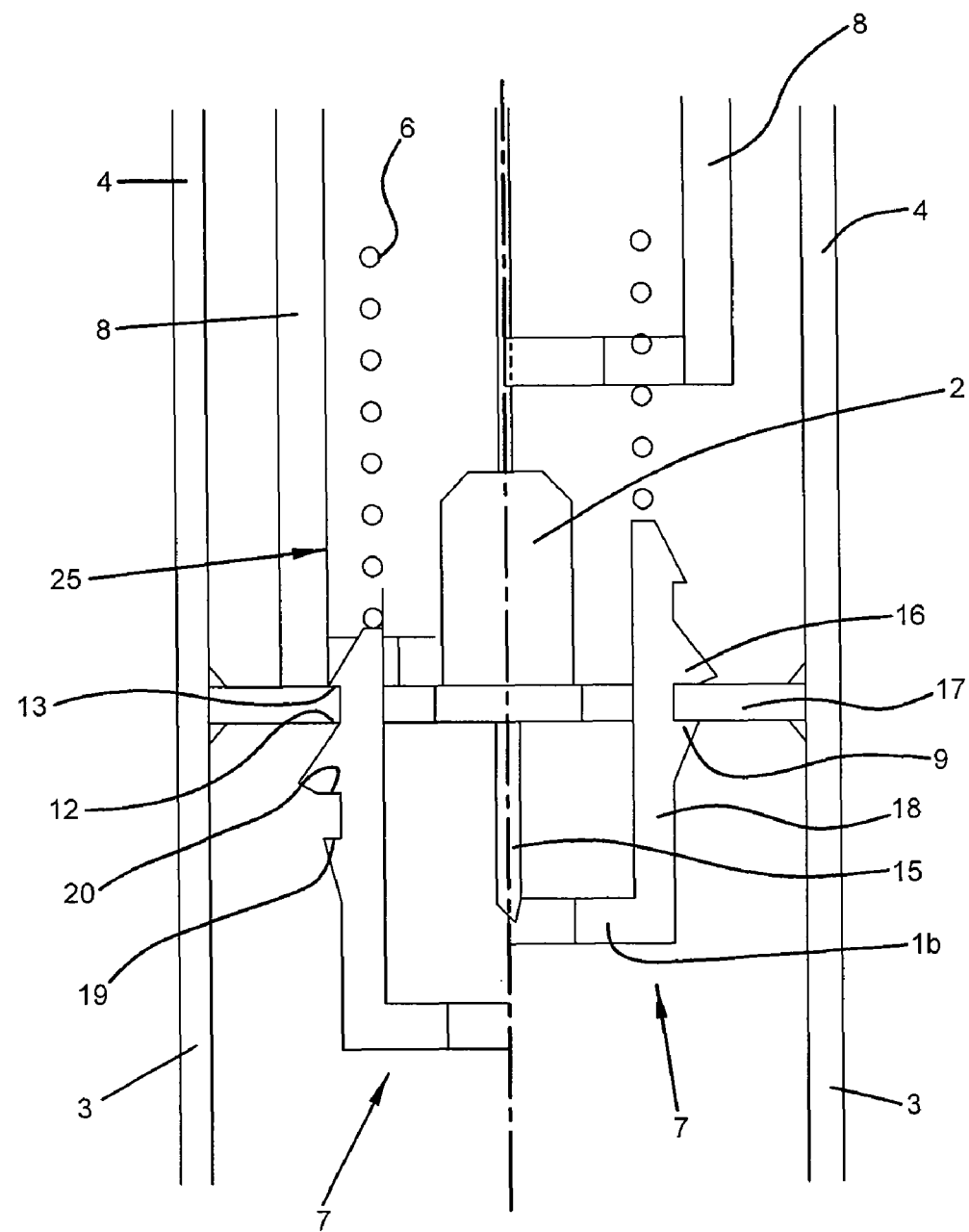
FIG. 16 is a diagram on a larger scale showing the lock mechanism, with the proximal needle guard in two different positions.

FIG. 16 illustrates two states of the components which co-operate to move the proximal needle guard 7. In the left-hand half of FIG. 16, the proximal needle guard 7 has assumed the distal initial position and in the right-hand half, the locked guard position. The left-hand half corresponds to the state illustrated in FIGS. 2 to 4 and FIG. 13 and the right-hand half of FIG. 16 corresponds to the state illustrated in FIG. 15.

In the initial position, the projections 16 hold the proximal needle guard 7 on the needle holder 2. The projections 17 taper in an arrow shape in the distal direction whilst the projections 18 taper in an arrow shape in the proximal direction. The stops 19 and 20 of the projections 17 and 18 are disposed axially facing one another. When the needle guard device is attached to an injection device by the fixing portion 3, for example is screwed on or clipped on, the proximal needle guard 7 moves into contact with the distal end of the injection device and is pushed in the distal direction against the force of the spring element 6 during the attachment operation. During this movement, the projections 17 slide by their arrow-shaped distal faces through the passages 11 of the needle holder 2 so that the locking elements 15 are bent elastically inward. As soon as the projections 17 have moved through the passages 11, they move into contact with the axial guide tracks 25 of the unlocking element 8. The locking elements 15 thus remain in the bent state, for which purpose the passages 11 offer a way of axially extending the guide tracks 25. The projections 17 extend farther outward than the following projections 18 which now move into the region of the passages 11. The extra distance of the projections 17 measured transversely to the longitudinal axis L is long enough for the projections 20 in contact with the guide tracks 25 to hold the locking elements 15 far enough away from the outer edge of the passages 11 to enable the projections 18 to be moved in the distal direction, likewise through the passages 11. Once the projections 18 have also moved through the passages 11, the proximal needle guard 7 moves farther in the distal direction due to the contact with the injection device until the proximal needle guard 7 assumes the releasing position illustrated in FIG. 14, once the connection to the injection device is established. At the same time as the injection device is attached, the needle connecting portion 1b pierces a sealing membrane on a distal end of a medicament reservoir and thus establishes a flow connection between the medicament reservoir and the proximal tip of the needle injection portion 1a.

When the needle guard device is detached from the injection device and pressure on the proximal needle guard 7 is thus released, the spring element 6 pushes the proximal needle guard 7 in the proximal direction. The proximal projections 18 firstly move into contact with the base 9 forming the locking element of the needle holder 2 so that the locking elements 15 are bent elastically inward again and the passages 11 are able to move in the proximal direction. As illustrated in FIG. 16, the guide track 25 of the unlocking element 8 may be sufficiently long in the axial direction to enable the projections 18 extending radially outward the farthest to pass the unlocking element 8 during the movement of the proximal needle guard 7 into the guard position. Alternatively, if the guide tracks 25 are short, as is the case with the exemplary unlocking element illustrated in FIGS. 8-15, the projections 18 are rounded at their outer ends or may be inclined, as in the embodiment illustrated as an example in FIG. 16 and also in FIGS. 12 and 14. In the end state after use illustrated in the right-hand half of FIG. 16, the projections 18 with their respective stop 19 in co-operation with the base or locking element 9 prevent the proximal needle guard 7 from being able to move in the distal direction again relative to the needle holder 2.

According to some embodiments, the needle guard device may be used as follows. The user attaches the needle guard device in the initial state illustrated in FIGS. 2 to 4 to an injection device by connecting the fixing portion 3 to the distal end of the injection device. During the connection process, the injection device pushes in the distal direction against the proximal needle guard 7, causing the latter to move into the releasing position illustrated in FIG. 14. At the same time, the injection needle 1 pierces the sealing membrane of the medicament reservoir in the region of its connecting portion 1b and establishes the flow connection to the proximal needle tip. When the needle guard device is attached to the injection device, the spring element 6 pushes the proximal needle guard 7 loosely against a point on the distal end of the injection device, for example against a terminal edge of the device or medicament reservoir. The distal needle guard 5 extends with its locking element 5a (FIG. 7) into the guide portion 4 so that the locking elements 5a are not able to fulfil any locking function in this state and the distal needle guard 5 is able to move freely against the force of the spring element 6 in the proximal direction.

For the actual injection, the user then places the injection device on the desired injection point on the skin by the distal end, which is now formed by the distal needle guard 5, and moves the injection device in the distal direction relative to the distal needle guard 5. The distal needle guard 5 moves under the pressing force and against the force of the spring element 6 in the proximal direction deeper into the guide portion 4. Simultaneously at the start of this movement, the ramp-shaped projections 5c of the distal needle guard 5 (FIG. 7) slide across the adapted ramp-shaped projections 24 of the unlocking element 8 (FIG. 8) so that its fingers 23 are elastically bent in the direction towards the central longitudinal axis L. During the remaining movement of the distal needle guard 5 in the proximal direction, the projections 24 slide in the axial direction across the internal face of the distal needle guard 5. During this sliding movement, the fingers 23 of the unlocking element 8 are constantly bent elastically inwardly and push against the internal face of the distal needle guard 5 with an elastic force. The distal needle guard 5 moves completely into the guide portion 4 so that the injection needle 1 penetrates the skin and the subcutaneous tissue by its entire injection portion 1a extending out from the guide portion 4. Full insertion of the distal needle guard 5 in the guide portion 4 may make the needle injection portion 1a as short as possible, but is not necessary.

After administering the medicament, the user moves the injection device away from the injection point so that the distal needle guard 5 moves back in the distal direction under the effect of the spring element 6. Since the unlocking element 8 is connected to the distal needle guard 5 due to a non-positive connection via the projections 24 and the elastically bent fingers 23, the distal needle guard 5 drives the unlocking element 8 with it as it moves in the distal direction so that the unlocking element 8 is lifted from the base 9 of the needle holder 2 and is moved relative to the proximal needle guard 7 into a neutral position. Since the projections 24 no longer extend through the distal needle guard 5, the distal needle guard 5 moves beyond the distal initial position relative to the guide portion 4 in the distal direction. As soon as the locking elements 5a of the distal needle guard 5 have passed the stops 4c of the guide portion 4 (FIG. 6), they snap outward into the recesses 4a and lock the distal needle guard 5 in a distal guard position, preventing a movement back in the proximal direction. The locating elements 5d move into the recesses 4d and co-operate with the stops 4e to hold the distal needle guard 5 on the guide portion 4. Instead of the unlocking element 8 holding the projections 24 on the distal needle guard 5 by only a non-positive connection (e.g., frictional contact), the engagement could also be based on a positive connection, in which case the unlocking element 8 would latch with the distal needle guard 5 by the projections 24. However, it the connection may be established early via the described non-positive connection.

To administer another injection, the user releases the needle guard device from the injection device with the distal needle guard 5 locked in its guard position. During the releasing process, the needle holder 2 moves in the distal direction relative to the injection device. The proximal needle guard 7 moves in the proximal direction relative to the needle holder 2 under the effect of the spring element 6. As soon as the projections 18 of the proximal needle guard 7 have passed the passages 11 in the base 9, i.e. the passages 11 of the locking element of the needle holder 2, the locking elements 15 of the proximal needle guard 7 snap elastically outward. In this state illustrated in the right-hand half of FIG. 16, the stops 20 of the big projections 17 hold the proximal needle guard 7 on the needle holder 2 against the force of the spring element 6 and the stops 19 of the proximal projections co-operating with the complementary stops 12 of the needle holder 2 prevent the proximal needle guard 7 from being able to move in the distal direction again. The two stops 19 and 20 clamp the base 9 of the needle holder 2 in a close fit between them, and the clearance is ideally just enough to ensure that the short snapping or pivoting movement of the locking elements 15 is not prevented. However, the play may be greater, provided allowance is made for the proximal needle guard 7 to move axially. Such an ability to move should not be so great that the distal tip of the injection needle 1 is able to project out from the proximal needle guard 7.

Figure 17:
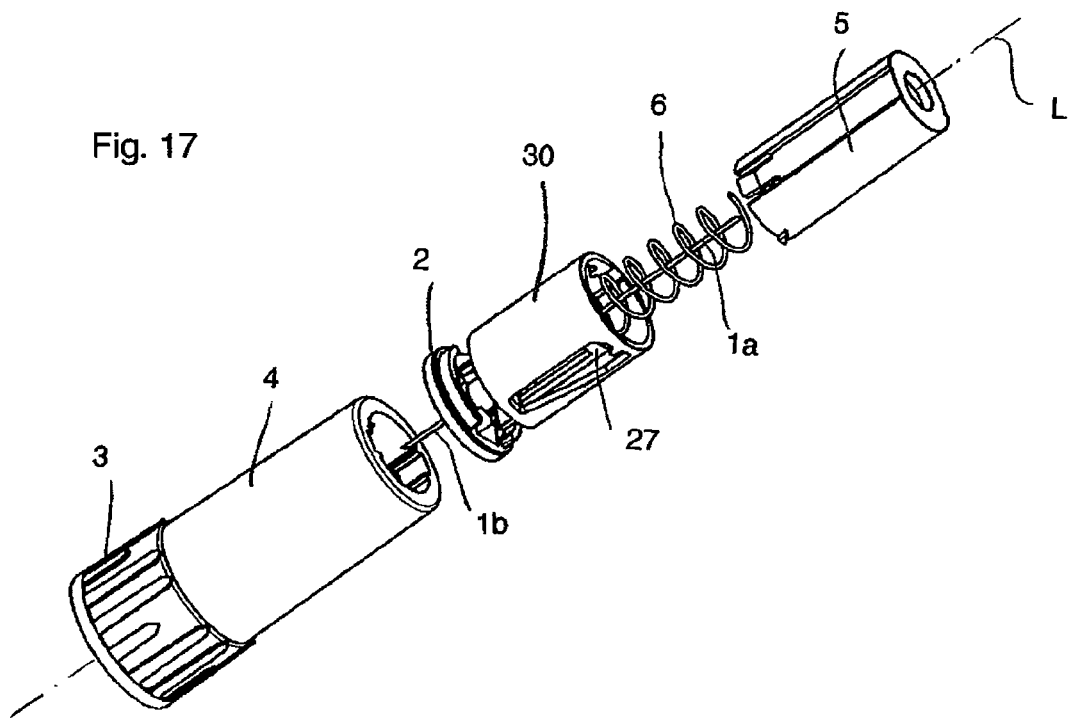
FIG. 17 shows components of a needle guard device based on a second embodiment in accordance with the present invention.

FIG. 17 shows a needle guard device based on a second embodiment with its components aligned longitudinally along a central longitudinal axis L in the order in which they are assembled. The needle guard device again comprises an injection needle 1 which is held by a needle holder 2, as was the case with the embodiment illustrated as a first example, a fixing and guide mechanism 3, 4 for attaching the needle guard device to the distal end of an injection device and providing an axial guide for a distal needle guard 5 as well as a spring element 6. As regards the way in which these components co-operate, the needle guard device of this embodiment corresponds to the embodiment illustrated as a first example. The fixing and guide mechanism is substantially similar to that described in connection with the first embodiment. The needle guard device also has a distal needle guard 27 and an unlocking element 30, which differ in terms of function from the same components 7 and 8 of the first embodiment, due to the way in which they co-operate with the other components.

Figure 18:
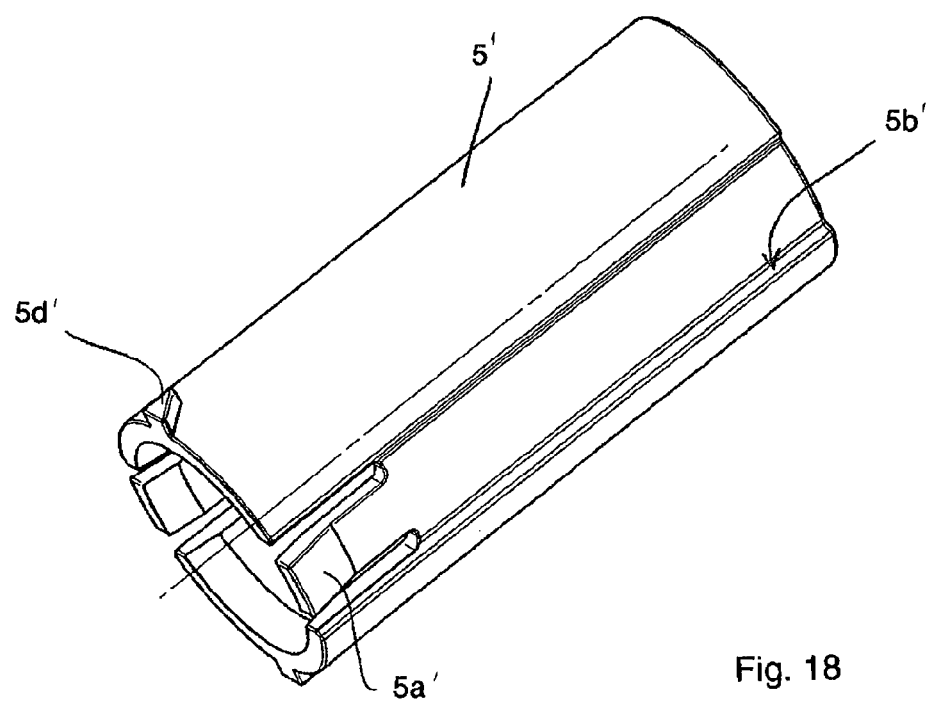
FIG. 18 shows the distal needle guard of the second embodiment.

FIG. 18 illustrates the distal needle guard 5' of the second embodiment. The distal needle guard 5' of the second embodiment is missing the two orifices with the projections 5c but otherwise corresponds to the distal needle guard 5 of the first embodiment except that there is a smaller geometric deviation in the case of the locating elements 5d'. The locating elements 5d' each have an inclination with respect to the longitudinal axis L on a side pointing in the circumferential direction about the longitudinal axis L so that the respective locating element 5a' forms a ramp at the relevant side.

FIGS. 19 and 20 illustrate the needle holder 2' of the second embodiment. The needle holder 2' again has a base 9' and a central retaining region 10' for an injection needle 1 to be arranged in base 9'. As with the first embodiment, the base 9' is provided with two passages 11' through which the needle guard 27 can move in the proximal direction into its guard position and which also serve as a means of locking the needle guard 27 in the guard position. Projecting outward from the base 9' in the distal direction adjacent to the retaining region 10' are two projections 26a offset from one another by 180° in the circumferential direction about the longitudinal axis L, each of which is inclined on one side to form a ramp. Facing the ramp-shaped, inclined sides of the projections 26a, a respective projection 26b also extends out from the base 9' in the distal direction. The plane of the section illustrated in FIG. 20 extends through the longitudinal axis L and through the gaps between each one of the projections 26a and the projection 26b facing the respective ramp.

FIG. 21 is a perspective view illustrating the unlocking element 30. FIG. 22 is a plan view showing a bottom face of the unlocking element 30, i.e. a view in the distal direction. The unlocking element 30 is of a hollow cylindrical design. Two recesses 31 are provided in the casing of the unlocking element 30 offset from one another by 180° in the circumferential direction, which extend through the casing and form a guide track 32 inclined on one side in the circumferential direction for one of the locating elements 5d' of the distal needle guard 5'. A respective projection 33 extends out from a distal edge of the unlocking element 30 into the respective recess 31. The two recesses 31 are circumferentially framed by the casing of the unlocking element 30 and a recess 35 is provided respectively on the internal face of the casing distally in front of the guide tracks 32 which extends from the distal end of the unlocking element 30 continuously into the respective recess 31. When the needle guard device is being assembled, the unlocking element 30 with its two recesses 35 is moved across the locating elements 5d' of the distal needle guard 5' so that the locating elements 5d' move into the respective co-operating recess 31. By turning the unlocking element 30, likewise during the course of assembly, the locating elements 5d' are then moved in the circumferential direction behind the respective projection 33 into the circumferential region 34 so that the locating elements 5d' locate behind the distal edge of the unlocking element 30 in its circumferential regions 34 and hold the distal needle guard 5' on the guide portion 4 against the force of the spring element 6 as a result. The unlocking element 30 is able to move in the distal direction so that it abuts with the guide portion 4 but is not able to move backward and forward between this abutting position and the base 9' of the needle holder 2', nor is it able to rotate relative to the needle holder 2' about the longitudinal axis L.

The unlocking element 30 has an annular base 36 projecting radially inwardly on its bottom face at the proximal end of its casing and locating elements 37 projecting out from the base 36 in the proximal direction, in total two locating elements 37, which are offset from one another by 180° in the circumferential direction. Two passages 38 for the proximal needle guard 27 are provided in the base 36, offset from one another by 180° in the circumferential direction.

Figure 23:
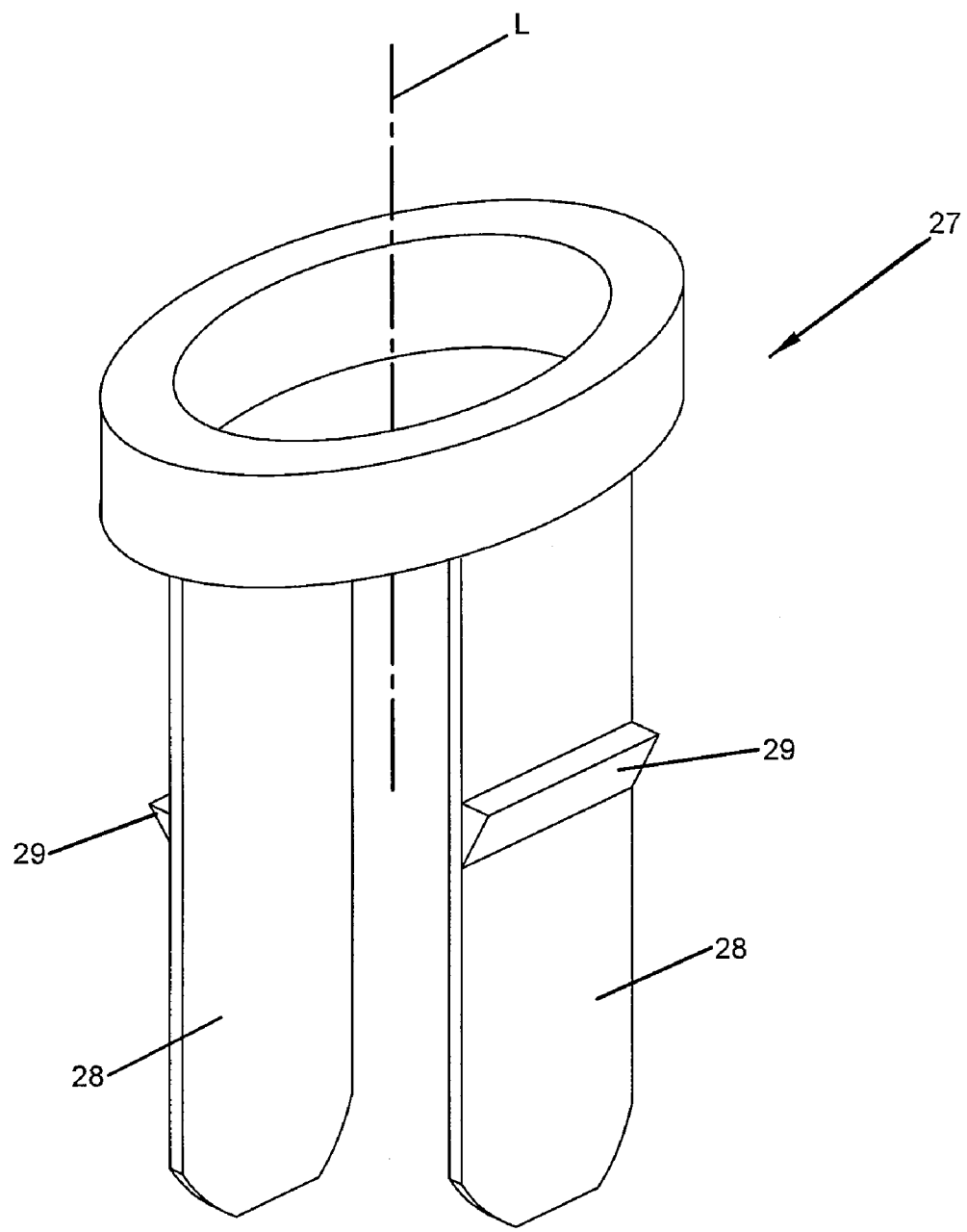
FIG. 23 shows a proximal needle guard of the second embodiment.

FIG. 23 illustrates the proximal needle guard 27. The needle guard 27 has an annular base at a distal end and flexible legs or fingers projecting elastically out from the base in the direction towards the longitudinal axis L, which constitute the locking elements 28 of the needle guard 27. A projection 29 is respectively formed on the external face of the locking elements 28. The projections 29 taper in an arrow shape in the proximal direction and, as was the case with the projections 17 of the first embodiment, respectively form a stop of the needle guard 27 pointing in the distal direction. In this respect, reference may be made to the explanation given in connection with the first embodiment.

Figures 24, 25:
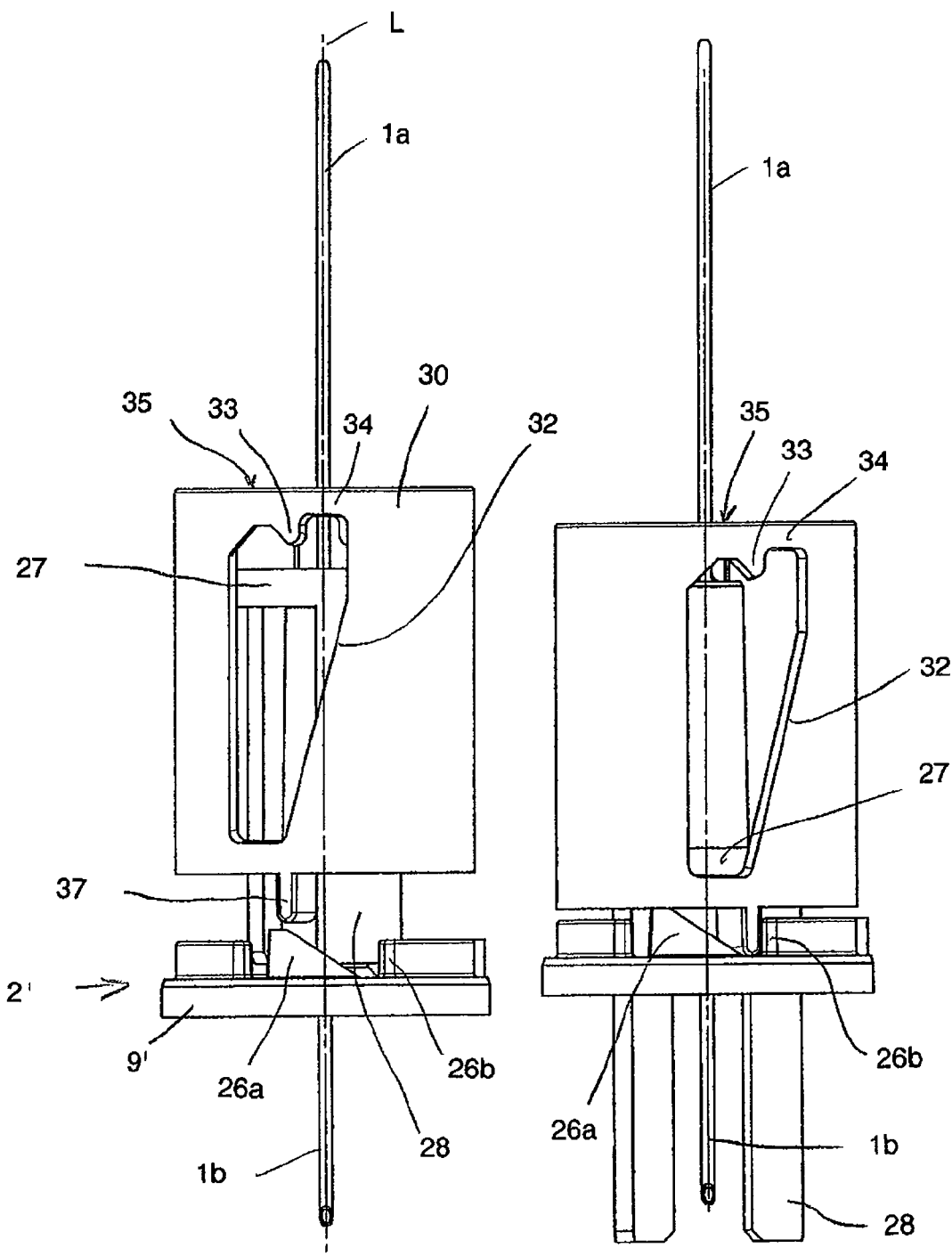
FIG. 24 shows a lock mechanism of the second embodiment in an initial state prior to an injection.
FIG. 25 shows the lock mechanism of the second embodiment in an end state after an injection.

FIG. 24 illustrates the components of the lock mechanism of the second embodiment which co-operate to lock the needle guard 27, with the needle guard 27 assuming a distal initial position which simultaneously also corresponds to the releasing position of the needle guard 27. In the second embodiment, when the needle guard 27 is in the initial position, it already is completely behind the connecting portion 1b of the injection needle 1 in the distal direction. It is also behind the base 9' of the needle holder 2', i.e. the spring element 6 pushes the needle guard 27 towards the base 9' in the proximal direction in the initial position. The locking elements 28 extend through the passages 38 of the unlocking element 30 (FIG. 22). When the needle guard device is in the initial state, the passages 38 and the passages 11 of the needle holder 2' are offset from one another in the circumferential direction. The locating elements 37 of the unlocking element 30 axially face the ramp-shaped sides of the projections 26a of the needle holder 2'. The spring element 6 holds the unlocking element 30 in the illustrated distal initial position illustrated in FIG. 24 via the distal needle guard 5' because the distal needle guard 5' locates behind the unlocking element 30 in the circumferential regions 34 by its locating elements 5d' and pulls it into the distal initial position, thereby moving it into abutment against the guide portion 4. This initial state is also illustrated in FIG. 26.

Figure 28:
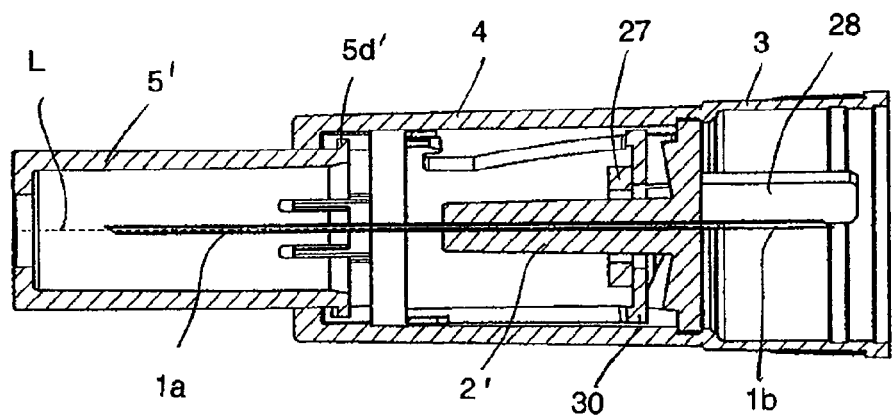
FIG. 28 shows the needle guard device of the second embodiment in the end state.

FIG. 25 illustrates the components of the lock mechanism in the end state after the needle guard device has been used and with the needle guard 27 disposed in its proximal guard position. FIG. 28 illustrates the needle guard device as a whole, likewise in its end state.

A description will be given below of how the needle guard device of the second embodiment works with reference to FIGS. 26 to 28 but also with reference to the other drawings of FIGS. 17 to 25, particularly FIGS. 24 and 25.

Figure 26:
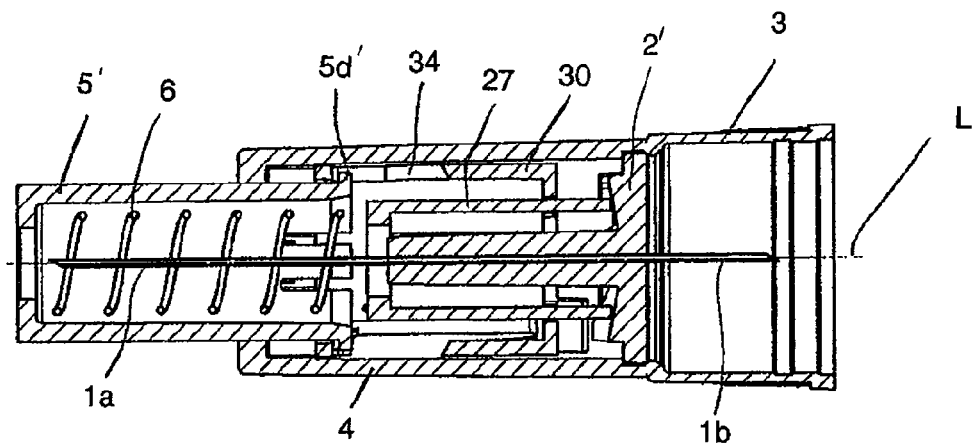
FIG. 26 shows the needle guard device of the second embodiment in the initial state.
Figure 27:
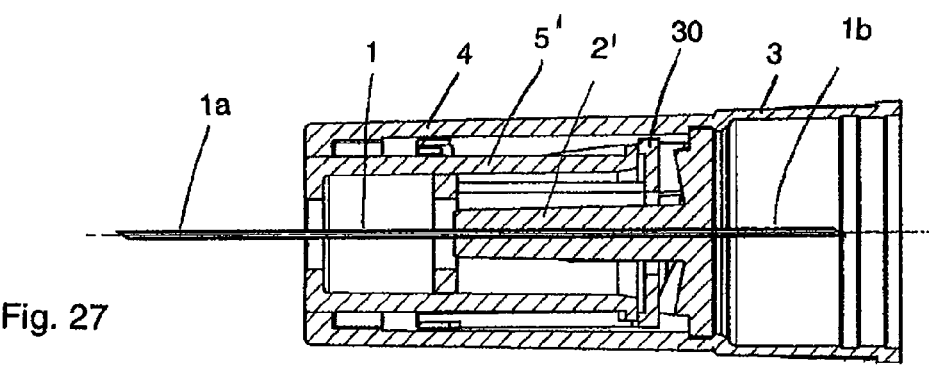
FIG. 27 shows the needle guard device of the second embodiment in a state during an injection.

The needle guard device is connected to the injection device in the initial state illustrated in FIGS. 24 and 26, for example screwed to it or clipped onto it. As this happens, the needle connecting portion 1b pierces the sealing membrane of the medicament reservoir. A movement of the needle guard 27 does not yet take place during the fitting process.

The user then pierces the skin through to the subcutaneous tissue at the desired injection point with the injection needle 1. As this happens, the distal needle guard 5' moves in the proximal direction relative to the needle holder 2' so that, conversely, the needle injection portion 1a projects forward. FIG. 27 illustrates the needle guard device in the piercing state whilst the medicament is being administered.

As the distal needle guard 5' moves in the proximal direction, the locating elements 5d' move along the respective associated guide track 32 of the unlocking element 30. The inclination of the guide track 32 is selected so that there is no or practically no inhibiting effect. As a result of this guide engagement, the unlocking element 30 is rotated out of its angular position illustrated in FIG. 24, the unlocking position, into the angular position (neutral position) illustrated in FIG. 25. The rotating movement is superimposed by an axial translating movement during which the locating elements 37 of the unlocking element 30 slide on the ramp-shaped side of the respective co-operating projection 26a. The translating and rotating movement is restricted by an abutting contact of the locating elements 37 and the projections 26b. The unlocking element 30 drives the needle guard 27 with it during the rotating movement because the locking elements 28 extend through the passages 38. As soon as the unlocking element 30 has reached its neutral position illustrated in FIG. 25, the passages 38 of the unlocking element 30 (FIG. 22) overlap the passages 11' of the needle holder 2' (FIGS. 19 and 20) to the degree that the locking elements 28 of the needle guard 27 are able to pass through the passages 11' due to the force of the spring element 6. The locking elements 28 are pushed by the spring element 6 against a point on the distal end of the injection device, for example a distal point of the device itself or the medicament reservoir. Once they have moved into the passages 11 of the needle holder 2, the locking elements 28 prevent the unlocking element 30 from being able to turn back into its unlocking position (FIG. 24).

When the injection needle 1 has been pulled out of the tissue and pressure has thus been relieved on the distal needle guard 5', the spring element 6 moves the distal needle guard 5 in the distal direction. The position of the two projections 33 in the circumferential direction relative to the respective facing guide track 32 is selected so that the locating elements 5d are able to move into the recesses 35 as the distal needle guard 5 moves in the distal direction, thereby causing the distal needle guard 5' to be finally released by the unlocking element 30, and the locking elements 5a' are able to move into the recesses 4a of the guide portion 4 (FIG. 6), as was the case with the first embodiment, and lock the distal needle guard 5' in its distal guard position to prevent it from moving in the proximal direction due to the lock engagement with the stops 4c. As with the first embodiment, the locating elements 5d co-operate with the stops 4e (FIG. 6) to ensure that the distal needle guard 5' can not be completely extracted from the guide portion 4 in the distal direction.

The needle guard device is released from the injection device with the distal needle guard 5' locked. The proximal needle guard 27 moves in the proximal direction relative to the needle holder 2' into the guard position illustrated in FIG. 25 and FIG. 26 under the effect of the spring element 6. In the guard position, the locking elements 28 extend beyond the tip of the needle connecting portion 1b in the proximal direction. The needle guard 27 is locked by a lock engagement between its projections 29 and the base 9' of the needle holder 2' to prevent a movement back in the distal direction. The needle guard 27 is supported by its annular base on the base 9' of the needle holder 2' in the proximal direction.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A needle guard device for use with an injection device, the needle guard device comprising:
   a) an injection needle comprising a needle injection portion extending to a distal end of the injection needle and a needle connecting portion extending to a proximal end of the injection needle;
   b) a needle holder comprising a retaining region through which a portion of the injection needle extends, a first end face from which the needle injection portion extends in a distal direction, and a second end face opposite from the first end face from which the needle connecting portion extends in a proximal direction;

c) a distal needle guard movably coupled to the needle holder, such that it can be moved from a releasing position in the distal direction into a guard position, the distal needle guard arranged behind the needle injection portion to expose the injection portion from the distal needle guard in the releasing position and overlaps the needle injection portion including the distal end of the injection needle in the guard position;

d) a proximal needle guard movably coupled to the needle holder, such that it can be moved from a releasing position in the proximal direction into a guard position, the proximal needle guard arranged behind the needle connecting portion to expose the needle connecting portion from the proximal needle guard in the releasing position and overlaps the needle connecting portion including the proximal end of the injection needle in the guard position; and e) a lock mechanism comprising a portion of the proximal needle guard and a portion of the needle holder for blocking a movement of the proximal needle guard out of its guard position into its releasing position;

f) wherein the needle guard device comprises a fixing sleeve configured to releasably attach the needle guard device to the injection device;

g) wherein the fixing sleeve forms an exterior of the portion of the needle guard device and said needle holder is fixedly arranged within the fixing sleeve; and h) wherein as the needle guard device is disconnected from the injection device, the proximal needle guard moves from the releasing position to the guard position, and the lock mechanism blocks the movement of the proximal needle guard out of its guard position.

2. The needle guard device of claim 1, wherein the proximal needle guard is arranged proximate to the needle connecting portion relative to the fixing sleeve.

3. The needle guard device of claim 2, wherein the fixing sleeve is configured to overlap the needle connecting portion, including the proximal end of the injection needle.

4. The needle guard device of claim 2, wherein the fixing sleeve surrounds the needle connecting portion and the proximal needle guard in its guard position.

5. The needle guard device of claim 1, further comprising a spring element configured to bias the proximal needle guard in the proximal direction by a spring force in order to move the proximal needle guard into the guard position.

6. The needle guard device of claim 5, wherein the spring element is configured to bias the distal needle guard in the distal direction by a spring force in order to move the distal needle guard into the guard position.

7. A needle guard device for use with an injection device, the needle guard device comprising:

a) an injection needle comprising a needle injection portion extending to a distal end of the injection needle and a needle connecting portion extending to a proximal end of the injection needle;

b) a needle holder comprising a retaining region through which a portion of the injection needle extends, a first end face from which the needle injection portion extends in a distal direction, and a second end face opposite from the first end face from which the needle connecting portion extends in a proximal direction;

c) a distal needle guard movably coupled to the needle holder, such that it can be moved from a releasing position in the distal direction into a guard position, the distal needle guard arranged behind the needle injection portion to expose the injection portion from the distal needle guard in the releasing position and overlaps the needle injection portion including the distal end of the injection needle in the guard position;

d) a proximal needle guard movably coupled to the needle holder, such that it can be moved from a releasing position in the proximal direction into a guard position, the proximal needle guard arranged behind the needle connecting portion to expose the needle connecting portion from the proximal needle guard in the releasing position and overlaps the needle connecting portion including the proximal end of the injection needle in the guard position; and e) a lock mechanism comprising a portion of the proximal needle guard and a portion of the needle holder for blocking a movement of the proximal needle guard out of its guard position into its releasing position, wherein the lock mechanism comprises a first locking element formed by a passage extending longitudinally through a radially projecting base of the needle holder and a second locking element formed by the proximal needle guard or connected to the proximal needle guard, and when the proximal needle guard is moved in the proximal direction, the second locking element is configured to slide through the first locking element passage and move into a lock engagement with the first locking element preventing a movement of the proximal needle guard in the distal direction when the proximal needle guard has reached the guard position, and when the proximal needle guard is in at least the guard position, the needle holder is not able to move in the proximal direction relative to the first locking element and the proximal needle guard is not able to move in the distal direction relative to the second locking element;

f) wherein the needle guard device is releasably attachable to the injection device.

8. The needle guard device of claim 7, wherein the first locking element forms a stop pointing in the proximal direction and the second locking element forms a stop pointing in the distal direction, and as the proximal needle guard moves in the proximal direction, the stop of the second locking element moves by the movement of the proximal needle guard in a proximal direction transversely to the longitudinal direction of the injection needle into an overlap, which prevents a movement of the proximal needle guard back into the releasing position.

9. The needle guard device of claim 7, wherein the passage formed in the needle holder further comprises a shoulder pointing in the proximal direction, which forms a proximal end of the passage, or is formed in the passage formed by the needle holder, and is configured as a stop of the first locking element.

10. The needle guard device of claim 9, wherein the second locking element is configured as a finger extending from the proximal to the distal end and is provided with a shoulder which acts as a stop for the first locking element.

11. The needle guard device of claim 7, wherein at least one of the locking elements is configured to move transversely to a longitudinal direction of the injection needle against a rebounding spring force which is based on a physical elasticity of the at least one of the locking elements.

12. The needle guard device of claim 7, wherein the proximal needle guard is configured as an arc around the needle connecting portion at a proximal or distal end, and the second locking element is configured in a finger shape and projects out from the arc in the distal or proximal direction.

13. The needle guard device of claim 7, wherein the lock mechanism comprises an unlocking element configured to move relative to the proximal needle guard and relative to the needle holder, from an unlocking position in which the unlocking element is arranged adjacent to the base of the needle holder such that the unlocking element blocks the second locking element from sliding through the first locking element and prevents the lock engagement, and into a neutral position in which the unlocking element moves distally relative to the base and permits the lock engagement.

14. The needle guard device of claim 13, wherein when the proximal needle guard is in the releasing position, or as the proximal needle guard is moving into the releasing position, the second locking element is configured to contact the unlocking element disposed in the unlocking position, which prevents the lock engagement.

15. The needle guard device of claim 13, wherein the distal needle guard is configured to move out of a distal initial position in the proximal direction as far as its releasing position and establishes an engagement with the unlocking element in the releasing position such that the unlocking element is carried to the neutral position as the distal needle guard moves to the guard position.

16. The needle guard device of claim 1, wherein the proximal needle guard comprises a proximal initial position in which the proximal needle guard overlaps the connecting portion prior to using the needle guard device, and wherein the proximal needle guard is moved from the proximal initial position into the released position as the needle guard device is connected to the injection device.

17. A needle guard device for use with an injection device, the needle guard device comprising:
  a) an injection needle comprising a needle injection portion extending to a distal end of the injection needle and a needle connecting portion extending to a proximal end of the injection needle:,
  b) a needle holder comprising a retaining region through which a portion of the injection needle extends, a first end face from which the needle injection portion extends in a distal direction, and a second end face opposite from the first end face from which the needle connecting portion extends in a proximal direction;
  c) a distal needle guard movably coupled to the needle holder, such that it is moved from a distal initial position in the proximal direction to a releasing position, and can be moved from the releasing position in the distal direction into a guard position, the distal needle guard overlapping the needle injection portion including the distal end of the injection needle in the distal initial position, is arranged behind the needle injection portion to expose the injection portion from the distal needle guard in the releasing position and overlaps the needle injection portion including the distal end of the injection needle in the guard position;
  d) a proximal needle guard movably coupled to the needle holder, such that it can be moved from a releasing position in the proximal direction into a guard position, the proximal needle guard arranged behind the needle connecting portion to expose the needle connecting portion from the proximal needle guard in the releasing position and overlaps the needle connecting portion including the proximal end of the injection needle in the guard position; and
  e) a lock mechanism comprising a portion of the proximal needle guard and a portion of the needle holder for blocking a movement of the proximal needle guard out of its guard position into its releasing position;
  f) wherein the needle guard device comprises a fixing sleeve configured to releasably attach the needle guard device to the injection device;
  g) wherein the fixing sleeve forms an exterior of the portion of the needle guard device and said needle holder is fixedly arranged within the fixing sleeve.

18. A needle guard device for use with an injection device, the needle guard device comprising:
  a) an injection needle comprising a needle injection portion extending to a distal end of the injection needle and a needle connecting portion extending to a proximal end of the injection needle;
  b) a needle holder comprising a retaining region through which a portion of the injection needle extends, a first end face from which the needle injection portion extends in a distal direction, and a second end face opposite from the first end face from which the needle connecting portion extends in a proximal direction;
  c) a distal needle guard movably coupled to the needle holder, such that it can be moved from a releasing position in the distal direction into a guard position, the distal needle guard arranged behind the needle injection portion to expose the injection portion from the distal needle guard in the releasing position and overlaps the needle injection portion including the distal end of the injection needle in the guard position;
  d) a proximal needle guard movably coupled to the needle holder, such that it can be moved from a releasing position in the proximal direction into a guard position, the proximal needle guard arranged behind the needle connecting portion to expose the needle connecting portion from the proximal needle guard in the releasing position and overlaps the needle connecting portion including the proximal end of the injection needle in the guard position, wherein the proximal needle guard extends through the needle holder at least in the releasing position from the proximal end to the distal end; and
  e) a lock mechanism comprising a portion of the proximal needle guard and a portion of the needle holder for blocking a movement of the proximal needle guard out of its guard position into its releasing position;
  f) wherein the needle guard device is releasably attachable to the injection device.

19. The needle guard device of claim 18, further comprising a spring element configured to bias the proximal needle guard in the proximal direction by a spring force in order to move the proximal needle guard into the guard position.

20. The needle guard device of claim 19, wherein the spring element is configured to bias the distal needle guard in the distal direction by a spring force in order to move the distal needle guard into the guard position.

21. The needle guard device of claim 18, wherein as the needle guard device is disconnected from the injection device, the proximal needle guard moves from the releasing position to the guard position, and the lock mechanism blocks the movement of the proximal needle guard out of its guard position.

22. The needle guard device of claim 21, wherein the proximal needle guard comprises a proximal initial position in which the proximal needle guard overlaps the connecting portion prior to using the needle guard device, and wherein the proximal needle guard is moved from the proximal initial position into the released position as the needle guard device is connected to the injection device.

23. The needle guard device of claim 17, further comprising a spring element configured to bias the distal needle guard in the distal direction by a spring force in order to move the distal needle guard into the guard position.

* * * * *